United States Patent [19]
Beremand et al.

[11] Patent Number: 5,021,343
[45] Date of Patent: Jun. 4, 1991

[54] METHOD FOR PRODUCING TRICHOTHECENES

[75] Inventors: Marian N. Beremand, Peoria, Ill.; Frank L. VanMiddlesworth, Fanwood, N.J.; Ronald D. Plattner, Goodfield, Ill.

[73] Assignee: The United States of America as represented by the Secretary of Agriculture, Washington, D.C.

[21] Appl. No.: 192,084

[22] Filed: May 10, 1988

[51] Int. Cl.$^5$ .................. C12P 17/18; C12N 1/14; C12N 1/38
[52] U.S. Cl. .................. 435/119; 435/254; 435/929; 435/244
[58] Field of Search ............... 435/254, 929, 119, 244

[56] References Cited
PUBLICATIONS

Bergers et al., *Appl. Environ. Microbiol.*, vol. 50, pp. 656–662, 1985.
Ueno et al., *Appl. Microbiol.*, vol. 30, pp. 4–9, 1975.
Beremand, *Appl. Environ. Microbiol*, vol. 53, pp. 1855–1859, 1987.
Stanbury et al., "Principles of Fermentation Technology", Pergamon Press, 1984, pp. 35–58.
Y. Ueno et al., "Biological and Chemical Detection of Trichothecene Mycotoxins of *Fursarium* Species", Appl. Microbiol. 25(4): 699–704, (Apr. 1973).
M. N. Beremand et al., "Effect of Leucine Auxotrophy on T-2 Toxin Biosynthesis: Production of Novel End--Products", Abstracts of Yeast Genetics and Molecular Biology, p. 93 (1986).

*Primary Examiner*—Douglas W. Robinson
*Assistant Examiner*—Irene Marx
*Attorney, Agent, or Firm*—M. Howard Silverstein; Curtis P. Ribando; John D. Fado

[57] ABSTRACT

Addition of L-leucine ot the fermentation medium of Fusarium mutant NRRL 18365 increases the production of the trichothecenes neosolaniol, 8-propionyl-neosolaniol, and 8-isobutyryl-neosolaniol. These materials are useful as toxins for the production of or investigation of immunotoxins for cancer therapy.

6 Claims, No Drawings

METHOD FOR PRODUCING TRICHOTHECENES

BACKGROUND OF THE INVENTION

Targeting the delivery of toxins to malignant cells by complexing the toxin to monoclonal antibodies which recognize the cancer cells is becoming an effective approach to cancer therapy. The toxin-monoclonal antibody conjugates preferentially bind to and selectively kill the cancer cells [D. A. Vallera et al., Science 222: 512 (1983); E. S. Vietetta et al., Science 238: 1098 (1987)].

The trichothecenes are a family of toxic fungal secondary metabolites which posses a characteristic 12,13-epoxy-trichothecene nucleus. The subsequent addition of several different oxygen-containing substituents to this nucleus leads to the production of over 60 different trichothecenes [C. Tamm and W. Breitenstein, In "The Biosynthesis of Mycotoxins," (Steyn, P. S., ed.), pp. 69–101, Academic Press, New York (1980)].

As a group, the trichothecenes appear to be promising toxins for the production of immunotoxins. The molecules are relatively small in size, and the class includes members with a wide range of toxic properties. Trichothecenes are potent inhibitors of protein synthesis [C. J. Carter and M. Cannon, Biochem. J. 166: 399–409 (1977); see also: Protection Against Trichothecene Mycotoxins, Natural Academy Press, Washington, DC, pp. 129–138 (1983)]. This diversity provides the potential to design anticancer agents to meet specific requirements. There is a medically important need for a variety of trichothecenes.

Prior to this time the trichothecenes neosolaniol, 8-propionylneosolaniol, and 8-isobutyryl-neosolaniol were available in relatively small amounts as minor components of fermentation broths [see M. N. Beremand, Abstracts of Yeast Genetics and Molecular Biology, p. 93 (1986); W. W. A. Bergers et al., Appl. Environ. Microbiol. 50: 656–662 (1985); A. Visconti et al., J. Assoc. Off. Anal. Chem. 70: 193–196 (1987)]. Structures of these materials are shown below.

| Trichothecene | R |
|---|---|
| Diacetoxyscirpenol (DES) | H |
| Neosolaniol [Compound (1), Neo] | OH |
| 8-Propionyl-neosolaniol [Compound (2), P-Neo] | $OCOCH_2CH_3$ |
| 8-Isobutyryl-neosolaniol [Compound (3), B-Neo] | $OCOCH(CH_3)_2$ |
| T-2 toxin | $OCOCH_2CH(CH_3)_2$ |

SUMMARY OF THE INVENTION

We have now unexpectedly discovered that addition of L-leucine to the fermentation broth of NRRL 18365, an ultraviolet-induced mutant of *Fusarium sporotrichioides* NRRL 3299, causes increased production of heretofore rare trichothecenes.

In accordance with this discovery, it is an object of the invention to produce relatively high yields of neosolaniol by a commercially feasible fermentation process.

A further object of the invention is to produce relatively high yields of 8-propionyl-neosolaniol by a commercially feasible fermentation process.

A further object of the invention is to produce relatively high yields of 8-isobutyryl-neosolaniol by a commercially feasible fermentation process.

Other objects and advantages of this invention will become readily apparent from the ensuing description.

BIOLOGICAL DEPOSIT

The leucine auxotroph of *Fusarium sporotrichiodes* described and claimed herein and referred to as "NRRL 18365" has been deposited under the Budapest Treaty in the Agricultural Research Culture Collection (NRRL) in Peoria, Ill., and has been assigned Accession Number NRRL 18365.

DETAILED DESCRIPTION OF THE INVENTION

The fungal strains used in this invention were derived by UV mutagenesis of *Fusarium sporotrichioides*, NRRL 3299 (ATCC 24043), deposited with the ARS Culture Collection, Peoria, IL. This strain was originally isolated from corn in France. The new mutant strain NRRL 18365 is also deposited with the ARS Culture Collection, Peoria, IL.

Microconidia were obtained for mutagenesis as follows. Frozen glycerol stocks of conidia were inoculated, after thawing, on agar plates, which were then incubated for several days. This resulted in cultures that produced primarily one- and two-celled microconidia. The microconidia thus obtained were then exposed to UV light and incubated in the dark for several days. Surviving colonies were then screened for L-leucine auxotrophy.

Using the above technique, a UV-induced leucine auxotroph NRRL 18365 was identified that produced compounds (1), (2), and (3) in concentrations of 28, 18, and 20 mg/L, respectively [Beremand, supra (1986)].

It has now been unexpectedly found that the addition of L-leucine to the fermentation broth of cultures of NRRL 18365 results in substantial increased production of the trichothecenes (1), (2), and (3).

In a typical fermentation procedure, a growth medium comprising glucose, 5–10%, preferably 5%; yeast extract, 0.1–0.2%, preferably 0.1%; peptone, 0.1–0.2%, preferably 0.1%, is prepared and inoculated with conidia to a level of $10^3$–$10^5$, preferably $5 \times 10^4$ per ml. L-leucine, 10 to 200 µg/ml, preferably 100 µg/ml, is added to the fermentation broth and the culture is incubated from 1 to 15 days, preferably 8 days, at 25°–30° C., preferably 28° C. Under these conditions, 80 to 150 µg/ml of compounds (1), (2), and (3) may be obtained.

Other conditions of fermentation and components of the growth medium will be obvious to those skilled in fermentation procedures.

The trichothecenes thus produced from NRRL 18365 may be isolated by standard techniques such as solvent extraction of the culture, including both cellular material and growth media, and subsequent purification by chromatographic procedures.

Table I shows the levels of trichothecenes produced by NRRL 18365 and the wild parent strain NRRL 3299 with and without added leucine.

The increased production of compounds (1), (2), and (3) by the leucine auxotroph allowed for their efficient isolation and characterization. Compounds (2) and (3) were identified as trichothec-9-ene-8α-propionyl-4β,15-acetyl-3αol (common name: 8-propionyl-neosolaniol or P-Neo) and trichothec-9-ene-8α-isobutyryl-4β,15-acetyl-3αol (common name: 8-iso-butyrylneosolaniol or B-Neo), respectively. P-Neo and B-Neo are related to T-2, with P-Neo containing a propionyl moiety and B-Neo containing an iso-butyryl moiety instead of the isovalerate at C8.

The structural similarity of these two compounds with T-2 was obvious from the GC-MS spectra of the TMS-derivatized crude (ETOAc) extract of the NRRL 18365 culture filtrate. All three compounds contain a common parent ion at m/z 377, which in each case arose from the loss of the C8 side chain moiety and one of the two acetates at either C4 or C15. Weak molecular ions were also observed for T-2-TMS (MH+, m/z 539), B-Neo-TMS (MH+, m/z 511), and the fragmentations were virtually identical below m/z 377.

Purification of the trichothecenes from the crude ethyl acetate extract was accomplished by using a combination of two chromatographic columns. Three trichothecene-containing fractions were obtained following chromatography on a silica gel column. One fraction consisted of purified (1), while the other two fractions contained a mixture of T-2, (2), (3), and DAS. These four compounds, which exhibit extremely similar chromatographic mobilities on normal phase particles, were separated via high-pressure liquid chromatography on a C-18 reverse phase column.

Definitive structures for B-Neo and P-Neo were derived from the spectral and chemical analyses of the purified compounds. Precise ammonia CI mass spectral analysis of the underivatized samples confirmed the hypothesized empirical formulae for B-Neo (MH$_4$+, m/z 470.2394, calc. for $C_{23}H_{36}NO_9$, 470.2388) and P-Neo (MH$_4$+, m/z 456.2241, calc. for $C_{22}H_{34}NO_9$, 456.2230). The basic carbon skeleton of the newly isolated compounds was chemically shown to be identical with each other and with that of T-2 by the hydrolysis (NH$_4$OH, CH$_3$OH) of each of the three to T-2 tetraol [identical by TLC or GC (TMS) with reference samples]. The $^1$H and $^{13}$C-NMR spectra of P-Neo, B-Neo, and T-2 are extremely similar and differ only in the alkyl regions (C-2', C-3', C-4', C-5', and associated protons), which corroborates the evidence that they are analogues. The only ambiguity left to be resolved was whether the C8 butyryl of B-Neo was n-butyryl or iso-butyryl. The fact that it is iso-butyryl can be ascertained from the observed $^1$H-NMR methyl doublet for C-3' and C-4' at 1.16 ppm (J=7 Hz). The $^{13}$C-NMR DEPT experiment also shows that the C8 side chain of B-Neo consists of two CH$_3$ groups and one CH, but lacks any CH$_2$ groups.

Without desiring to be bound by any theory of operation, it is believed that the preliminary results with the leucine auxotroph suggest that the biosynthesis of T-2 is dependent upon leucine and that leucine deprivation results in the utilization of alternative branch pathways. These possibilities were further examined by testing whether trichothecene production could be altered by varying the leucine concentration in the growth medium.

Growth and trichothecene production were measured in wild type and Leu⁻ cells cultured in complete medium without additional leucine and supplemented with up to 100 μg/ml leucine. Neither the wild type nor the Leu⁻ mutant showed any change in growth rate in response to the different levels of leucine. Likewise, the pattern, kinetics, and level of trichothecene production remained constant in the wild type culture over the time period and the range of leucine concentrations tested. This was not observed for the Leu⁻ mutant. The leucine concentration in the medium not only dramatically affected the pattern of trichothecene production by the Leu⁻ mutant, but also the kinetics and level of production.

In the leucine auxotroph, the proportion of the T-2 analogues (Neo, P-Neo, and B-Neo) are inversely related to the proportion of T-2 and the concentration of leucine in the medium. At the highest concentration, the wild type ratio of DAS:Neo:P-Neo:B-Neo:T-2 was approached; 100 μg/ml additional leucine initially shifted the percent of DAS:Neo:P-Neo:B-Neo:T-2 in NRRL 18365 from approximately 4:18:19:19:40 to 3:8:10:7:72, which is closer to the wild type percentages of approximately 2:7:5:4:82. Values obtained for 10 μg/ml and 50 μg/ml additional leucine followed a similar shift, but at levels that corresponded to the leucine concentration. At all leucine concentrations, the steady decrease in the relative proportions of T-2 with increasing growth time most likely reflects a progressive exhaustion of leucine from the medium. The above results support the hypotheses that leucine is a precursor to T-2 and that, in response to leucine deprivation, alternative pathways are utilized which lead to the production of T-2 analogues.

In addition, the kinetics and level of total trichothecene production are directly related to the leucine concentration in the medium. At 0 and 10 μg/ml leucine, total toxin production was less for NRRL 18365 than the wild type parent, but, at 50 and 100 μg/ml additional leucine, total toxin production exceeded that of the wild type parent.

The data reported in Table I tabulate the yields (in mg/L) of the individual toxins produced by the wild type and mutant strains at the minimum and maximum leucine concentrations tested. Under the appropriate conditions, the leucine auxotroph can be expected to produce a minimum of 66 mg/L Neo, 36 mg/L P-Neo, and 35 mg/L B-Neo.

The following examples are intended only to further illustrate the invention and are not intended to limit the scope of the invention, which is defined by the claims.

EXAMPLE 1

UV Mutagenesis and Mutant Screen

Microconidia were obtained from V-8 agar plates that were incubated for 4 days following inoculation with approximately 2.5×10⁶ freshly thawed conidia from frozen (−70° C.) glycerol stocks. This procedure yielded primarily one- and two-celled microconidia, with approximately 65% of the total being one-celled. The microconidia were exposed to UV light (254 nm) on agar plates until 90% kill was achieved [See J. Avalos et al., Appl. Environ. Microbiol. 49: 187–191 (1985) and M. N. Beremand, Appl. Environ. Microbiol. 53: 1855–1859 (1987)].

The UV-treated plates were immediately placed in the dark and incubated for 2 to 3 days in the growth chamber. The following components were used in the medium for the isolation of mutants: M-100 minimal medium (10 g of glucose, 3 g of KNO$_3$, 20 g of agar, 62.5 ml of salt solution, 937.5 ml of deionized water; salt solution [16 g of KH$_2$PO$_4$, 4 g of Na$_2$SO$_4$, 8 g of KCl, 2 g of $MgSO_4.2H_2O$, 1 g of $CaCl_2$, 8 ml of trace elements solution, deionized water to 1 liter]; trace element solution [30 mg of $H_3BO_3$, 70 mg of $MnCl_2.4H_2O$, 422 mg of $ZnSO_4.7H_2O$, 20 mg of $Na_2MoO_4.2H_2O$, 30 mg of $FeCl_3$, 200 mg of $CuSO_4.5H_2O$, 500 ml of deionized water]; M-100 supplemented with adenine (40 μg/ml), uracil (40 μg/ml), and 20 amino acids (40 μg/ml each); and 0.3% yeast extract, 1.0% peptone, 2.0% glucose, 2.0% agar, 0.05% (vol/vol) Triton X-100 (YEPD-2G-5T). To screen for auxotrophy, strains were tested for their ability to grow on M-100 minimal medium. Those that failed to grow were tested further for adenine, uracil, or amino acid growth requirements by standard methods.

EXAMPLE 2

Culture Growth Conditions

Cultures were grown on V-8 complete agar medium usually supplemented with 40 μg/ml L-leucine slants or plates on an alternating 12-hr 25° C. light/20° C. dark schedule. For long-term storage, strains were maintained on V-8 complete agar plus leucine slants at 4° C. and were stored as conidial suspensions in 10 to 15% (vol/vol) glycerol at −90° C. For all assays, fresh transfers of the strains were obtained from stock cultures stored at 4° C.

Trichothecene production was measured in liquid shake cultures. Conidial suspensions were prepared from 1- to 2-week-old cultures grown on V-8 complete agar plus leucine plates. 2.8-Liter Fernbach flasks containing 1 L of 5% glucose-0.1% yeast extract-0.1% peptone and 100 μg/ml L-leucine were inoculated with conidia to a final concentration of $10^4$ per ml. Cultures were incubated at 200 rpm on a gyratory shaker. Incubation was continued as described above for a total of 8 days, at which time the products were isolated and analyzed.

EXAMPLE 3

Analysis of Trichothecenes

Aliquots (5 ml) of the cultures, or culture filtrates, were extracted with ethyl acetate (EtOAc, 3×10 ml); the combined EtOAc extracts were filtered through a charcoal column (Romer Labs) and eluted under slight vacuum (600 mm HG pressure). The columns were eluted with additional EtOAc (2×10 ml) and the EtOAc was removed from the pooled eluents at 35° C. in vacuo; the resulting residue was dissolved in 2 ml of toluene: acetone: methanol (2:1:1) and 400 μl aliquots were evaporated to dryness. Trimethylsilyl (TMS) derivatives were prepared for gas chromatography (GC) or gas chromatography-mass spectrometry (GC-MS) analysis by treating the above residues with 100 μl of Tri-Sil/TBT (Pierce Chemical Co., Rockford, IL) at 80° C. for 1 hr. The derivatized samples were then diluted to 1 ml with hexane. For GC analysis, 2 μl of the derivatized samples were injected (in the splitless mode) onto a Spectra Physics 7100 GC equipped with a flame ionization detector, and a 30 m ×0.25 mm DB-1 coated (0.25 micron) capillary column (J. & W. Scientific, Folsom, GA). The temperature program consisted of an initial over temperature of 120° C., followed by a 15° C./min gradient to 210° C. with 1 min at 210° C., and a 5° C./min gradient to 260° C. with an additional 10 min at 260° C. The retention times (in min) observed were: DAS, 12.37; Neo, 14.68; P-Neo, 16.1; B-Neo, 16.5; and T-2, 17.9. For GC-MS analysis, the derivatized sample was chromatographed using a 30 m×0.225 mm DB-1 capillary column (J. & W. Scientific) which was coupled directly to the source of a Finnigan TSQ 46 mass spectrometer. Spectra were recorded in the electron ionization (EI) mode or the chemical ionization (CI) mode. For CI spectra, isobutane (0.3 torr) was the reagent gas and the temperature was 100° C. Precisely measured, high resolution mass spectra were obtained from analysis of pure samples inlet via the solids probe into a VG 7070 mass spectrometer and analyzed in the CI mode with ammonia as the reagent gas. T-2, DAS, Neo, and T-2 tetraol standards were obtained from Sigma (St. Louis, Mo.).

EXAMPLE 4

Isolation of P-Neo and B-Neo

P-Neo and B-Neo were isolated from a 4-L fermentation of NRRL 18365. Using the procedures described above, four replica 1-L liquid cultures in 2-L flasks were inoculated to a final density of $1 \times 10^4$ conidia/ml. After 8 days incubation at 28° C. and 200 rpm, each 1-L culture was extracted with EtOAc (3×400 ml), and the combined organic solvents derived from all four cultures were removed in vacuo, leaving 1.15 g of crude residue. The residue was applied to a silica gel (250 g) column. The column was then washed with 200 ml $CH_2Cl_2$, and the trichothecenes were eluted with 3×500 ml ethyl acetate. The final fraction, eluted with methanol (400 ml), contained no trichothecenes and was discarded. The residue (665 mg) obtained from concentration of the combined EtOAc fractions was divided into two portions of 265 mg and 400 mg. Exploratory methods of purification were performed with the 265-mg portion, and the 400-mg portion was purified by preparatory RP-HPLC in batches of 60 mg each. The 400-mg fraction gave rise to purified compound (1) or P-Neo (36 mg) and compound (2) or B-Neo (43 mg). The HPLC chromatography was conducted on a Spectra Physics 8100 HPLC equipped with a C-18 reverse phase Rainin Dynamax column (30 cm×21.4 mm i.d.). An isocratic solvent system of $CH_3OH:H_2O$ (60:40) was used at a flow rate of 6 ml/min, and the column was held at 50° C. The trichothecenes were detected by their UV absorption at 210 nm using a Spectra Physics 8440 UV detector. Under these conditions the following retention times (in min) were observed: DAS, 19.7; P-Neo, 21.5; B-Neo, 33.4; and T-2, 54.8.

It is understood that the foregoing detailed description is given merely by way of illustration and that modification and variations may be made therein without departing from the spirit and scope of the invention.

TABLE I

| | Level of Trichothecene Production by Wild Type NRRL 3299 and Leu NRRL 18365 Strains of *Fusarium sporotrichioides*[a] | | | | | | |
|---|---|---|---|---|---|---|---|
| Strain | Added [leu] (μg/ml) | DAS | Neo | P-Neo (μg/ml) | B-Neo | T-2 | Total (μM) |
| NRRL 3299 | 0 | 5 | 15 | 4 | 4 | 141 | 374 |
| | 100 | 6 | 18 | 4 | 5 | 150 | 378 |

TABLE I-continued

Level of Trichothecene Production by Wild Type NRRL 3299 and Leu NRRL 18365 Strains of *Fusarium sporotrichioides*[a]

| Strain | Added [leu] (μg/ml) | DAS | Neo | P-Neo (μg/ml) | B-Neo | T-2 | Total (μM) |
|---|---|---|---|---|---|---|---|
| NRRL 18365 | 0 | 8 | 44 | 21 | 20 | 43 | 320 |
|  | 100 | 11 | 67 | 37 | 36 | 89 | 558 |

[a]All values represent amount present in 8-day-old liquid shake cultures and are averages from duplicate cultures, except for NRRL 3299 at 0 μl/ml leucine which is from a single culture.

We claim:

1. A method of producing trichothecenes selected from the group consisting of neosolaniol, 8-propionyl-neosolaniol and 8-isobutyryl-neosolaniol comprising fermenting a culture medium containing L-leucine with a leucine auxotroph having all the identifying characteristics of *Fusarium sporotrichiodes* ARS Culture Collection Accession No. NRRL 18365 and mutants thereof, wherein said auxotroph and mutants have the capability of producing and accumulating higher levels of neosolaniol, 8-propionyl-neosolaniol and 8-isobutyryl-neosolaniol than the wild type parent strain *Fusarium sporotrichiodes* NRRL 3299 from which the auxotroph is derived, and recovering said trichothecenes from the culture medium.

2. A method as described in claim 1 wherein said trichothecene is neosolaniol.

3. A method as described in claim 1 wherein said trichothescene 8-propionyl-neosolaniol.

4. A method as described in claim 1 wherein said trichothecene 8-isobutyryl-neosolaniol.

5. A method as described in claim 1 wherein said L-leucine concentration is between 10 to 200 μg/ml.

6. A leucine auxotroph having all the identifying characteristics of *Fusarium sporotrichiodes* ARS Culture Collection Accession No. NRRL 18365 and mutants thereof; wherein said auxotroph and mutants have the capability of producing and accumulating substantially higher levels of neosolaniol, 8-propionyl-neosolaniol and 8-isobutyryl-neosolaniol, than the wild type parent strain *Fusarium sporotrichiodes* NRRL 3299 from which the auxotroph is derived.

* * * * *